US012606176B2

(12) United States Patent

Huh

(10) Patent No.: US 12,606,176 B2

(45) Date of Patent: Apr. 21, 2026

(54) ELECTRIC VEHICLE AND A METHOD FOR CONTROLLING THE SAME

(71) Applicants: HYUNDAI MOTOR COMPANY, Seoul (KR); KIA CORPORATION, Seoul (KR)

(72) Inventor: Jee Wook Huh, Seoul (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 182 days.

(21) Appl. No.: 18/500,452

(22) Filed: Nov. 2, 2023

(65) Prior Publication Data

US 2024/0425059 A1      Dec. 26, 2024

(30) Foreign Application Priority Data

Jun. 23, 2023    (KR) ........................ 10-2023-0081290

(51) Int. Cl.
  *B60W 40/08* (2012.01)
  *A61B 5/18* (2006.01)
  (Continued)

(52) U.S. Cl.
  CPC .............. *B60W 40/08* (2013.01); *A61B 5/18* (2013.01); *B60H 1/00742* (2013.01); *B60L 58/12* (2019.02); *B60W 2040/0827* (2013.01)

(58) Field of Classification Search
  CPC ......... B60W 40/08; B60W 2040/0827; B60W 10/06; B60W 10/08; B60W 10/26; B60W 10/30; B60W 50/14; B60W 2510/0676; B60W 2510/244; B60W 2540/215; B60W 2540/221; B60W 2540/229; B60W 2710/0688; B60W 2710/244; B60W 20/12; B60W 20/10; A61B 5/18; A61B 5/369; A61B 5/4809; A61B 5/6893; B60H 1/00742; B60L 58/12; B60L 3/00; B60L 2240/34; B60L 2240/60; B60L 2250/12; G01C 21/3469; G01C 21/3617; (Continued)

(56) References Cited

U.S. PATENT DOCUMENTS 5,390,728 A * 2/1995 Ban ................... B60H 1/00842
                                                165/204
11,414,031 B2 * 8/2022 Vijithakumara ........ B60R 16/03
(Continued)

FOREIGN PATENT DOCUMENTS

JP      2015131521 A      7/2015
JP      2019131109 A      8/2019

*Primary Examiner* — Fadey S. Jabr
*Assistant Examiner* — Faris Asim Shaikh
(74) *Attorney, Agent, or Firm* — Lempia Summerfield Katz LLC

(57) ABSTRACT

An electric vehicle may include logic for drowsiness prevention via brain wave analysis of a driver. A method for controlling the electric vehicle may include determining whether a driver needs to sleep based on a result of analyzing a brain wave of the driver. The method may also include changing a destination to a sleeping area based on selection of the driver when it is determined that the driver needs to sleep. The method may further include controlling a state of charge of a battery during travel to the sleeping area or after stopping at the sleeping area and controlling a sleep environment.

19 Claims, 9 Drawing Sheets

(51) Int. Cl.
  B60H 1/00 (2006.01)
  B60L 58/12 (2019.01)

(58) Field of Classification Search
  CPC . B60Y 2200/91; B60Y 2200/92; Y02T 10/62;
           Y02T 10/70; Y02T 10/7072; Y02T 10/72
  See application file for complete search history.

(56) References Cited

U.S. PATENT DOCUMENTS

| | | | | |
|---|---|---|---|---|
| 2006/0226246 A1* | 10/2006 | Rohm | ............... | B60H 1/00735 |
| | | | | 237/12.3 R |
| 2009/0069963 A1* | 3/2009 | Kobayashi | ............. | B60L 58/40 |
| | | | | 701/22 |
| 2012/0152512 A1* | 6/2012 | Mori | .................. | B60H 1/00864 |
| | | | | 165/202 |
| 2012/0169142 A1* | 7/2012 | Lee | .................... | B60C 23/0459 |
| | | | | 307/130 |
| 2013/0226389 A1* | 8/2013 | Yamazaki | ............. | B60W 10/26 |
| | | | | 701/22 |
| 2014/0144998 A1* | 5/2014 | Ichishi | .................... | B60H 1/08 |
| | | | | 237/12.3 A |
| 2014/0229059 A1* | 8/2014 | Surnilla | ............. | B60H 1/00742 |
| | | | | 701/1 |
| 2016/0288784 A1* | 10/2016 | Teraya | ................... | B60K 6/442 |
| 2016/0361515 A1* | 12/2016 | Jung | ................. | A61B 5/02055 |
| 2017/0343367 A1* | 11/2017 | Lee | ........................ | A61B 5/204 |
| 2018/0030865 A1* | 2/2018 | Amin | ..................... | B60K 6/445 |
| 2018/0072310 A1* | 3/2018 | Fung | .................... | B60W 50/14 |
| 2018/0081374 A1* | 3/2018 | Nimchuk | ......... | G06Q 10/08355 |
| 2018/0117989 A1* | 5/2018 | Min | ................... | B60H 1/00807 |
| 2019/0031175 A1* | 1/2019 | Lee | ........................ | B60W 20/12 |
| 2020/0182635 A1* | 6/2020 | Zender | .............. | G01C 21/3415 |
| 2020/0353933 A1* | 11/2020 | Gilbert | ............... | B60W 30/192 |
| 2022/0107191 A1* | 4/2022 | Diamond | .............. | G06Q 50/40 |
| 2023/0278449 A1* | 9/2023 | Kinsey | ................... | B60L 53/62 |
| | | | | 701/22 |
| 2024/0092339 A1* | 3/2024 | Hirata | ................ | B60W 30/192 |
| 2024/0108263 A1* | 4/2024 | Pickett | ................... | A61B 5/746 |

* cited by examiner

S320

S50

ELECTRIC VEHICLE AND A METHOD FOR CONTROLLING THE SAME

CROSS-REFERENCE TO RELATED APPLICATION

This application claims the benefit of and priority to Korean Patent Application No. 10-2023-0081290, filed on Jun. 23, 2023, the entire contents of which are incorporated herein by reference.

TECHNICAL FIELD

The present disclosure relates generally to an electric vehicle, and more specifically, to an electric vehicle and a method for controlling the same that identify drowsiness of a driver via analysis of a brain wave of the driver, prevent accidents by inducing sleep after stopping, and include a battery usage strategy for creating an optimal sleep environment and minimizing power consumption.

BACKGROUND

With development in science and technology, vehicles have become important means of transportation for mankind in modern society. In the past, fossil fuel has been mainly used as an energy source for the vehicles. More recently, vehicles using electricity or hydrogen as an energy source have been developed in preparation for exhaustion of the fossil fuel.

Traffic accidents are one of many problems that occur as numerous vehicles travel on a road. One of main causes of such traffic accidents is drowsy driving of a driver. To prevent such drowsy driving, vehicles equipped with a drowsiness notification function have been developed. However, typical vehicles equipped with the drowsiness notification function only use the drowsiness notification function via time setting or use a function of determining whether the driver is drowsy via a camera. In such a typical vehicle equipped with the drowsiness notification function, it is difficult to determine whether the driver is actually drowsy.

To prevent accidents caused by drowsy driving of the driver, sleeping areas such as rest areas are provided, but this also follows a premise that the driver must voluntarily recognize the drowsy state and move to the sleeping area. Moreover, sleep environment at the sleeping areas is not good because of noise and vibration caused by repeated turning on and off of a vehicle engine when the driver sleeps after moving to the sleeping area and stopping.

A battery used in an electric vehicle has an advantage of producing less noise and vibration compared to an internal combustion engine used in a conventional vehicle. However, a battery has a disadvantage in that the battery drains quickly because of various electric loads, so that it is difficult to provide a quality sleep environment for a long time.

SUMMARY

The present disclosure has been made to solve the above-mentioned problems occurring in the prior art while advantages achieved by the prior art are maintained intact.

Embodiments of the present disclosure effectively prevent accidents by determining whether a driver is actually drowsy via a brain wave analysis function and guiding the driver to a sleeping area.

Embodiments of the present disclosure control an optimal sleep environment and reduce unnecessary battery consumption using a battery with less noise and vibration during sleeping after stopping at a sleeping area in an electric vehicle that uses an engine and the battery at the same time.

The technical problems to be solved by the present disclosure are not limited to the aforementioned problems, and other technical problems not mentioned herein should be clearly understood from the following description by those having ordinary skill in the art to which the present disclosure pertains.

According to an embodiment of the present disclosure, a method for controlling an electric vehicle is provided. The method includes determining whether a driver needs to sleep based on a result of analyzing a brain wave of the driver. The method also includes changing a destination to a sleeping area based on selection of the driver when it is determined that the driver needs to sleep. The method further includes securing a state of charge of a battery necessary for movement to the sleeping area and the sleep of the driver.

In an aspect, determining whether the driver needs to sleep may include providing a sleep consent notification.

In an aspect, the sleeping area may be a sleeping area within a predetermined range based on a current location.

In an aspect, securing the state of charge of the battery may include determining whether to charge the battery based on a predetermined threshold value.

In an aspect, securing the state of charge of the battery may include calculating an amount of energy required for charging when the battery needs to be charged.

In an aspect, securing the state of charge of the battery may include determining a time point for turning on an engine to charge the battery.

In an aspect, the method may further include controlling an indoor temperature of the electric vehicle and a temperature of cooling water.

In an aspect, controlling the temperatures may include controlling the indoor temperature to a temperature lower than a target indoor temperature when the indoor temperature needs to be lowered.

In an aspect, controlling the temperatures may include controlling the temperature of the cooling water to a temperature higher than a target cooling water temperature when the indoor temperature needs to be increased.

In an aspect, the method may further include reducing or minimizing power consumption by selecting a controller unnecessary when controlling a sleep temperature of the driver.

In an aspect, minimizing the power consumption may be performed after travel of the electric vehicle is ended.

According to another embodiment of the present disclosure, a hybrid electric vehicle is provided. The hybrid electric vehicle includes a brain wave analyzer configured to determine whether a driver needs to sleep based on a result of analyzing a brain wave of the driver. The hybrid electric vehicle also includes an information output device configured to change a destination to a sleeping area and guides the sleeping area when the driver needs to sleep. The hybrid electric vehicle additionally includes a battery controller configured to control a state of charge of a battery necessary for movement to the sleeping area and maintaining a sleep environment of the driver.

In an aspect, the information output device may be configured to provide a sleep necessity notification when the driver needs to sleep.

In an aspect, the information output device may be configured to search for a sleeping area within a predetermined range based on a current location and provide the found sleeping area to the driver when the driver needs to sleep.

In an aspect, the battery controller may be configured to calculate an amount of energy required for charging of the battery when a current state of charge of the battery is smaller than a predetermined threshold value.

In an aspect, the hybrid electric vehicle may further include an engine controller configured to control an operation of an engine for producing the energy to be charged to the battery. The battery controller may be configured to determine a time point for turning on the engine based on the calculated amount of energy for the charging.

In an aspect, the hybrid electric vehicle may further include a temperature controller configured to control an indoor temperature of a room where the driver is located and a temperature of cooling water of the hybrid electric vehicle.

In an aspect, the temperature controller may be configured to set a target indoor temperature based on the indoor temperature of the room where the driver is located and an external temperature of the hybrid electric vehicle.

In an aspect, the temperature controller may be configured to perform control to increase the temperature of the cooling water when the indoor temperature needs to be increased.

In an aspect, the hybrid electric vehicle may further include an engine controller configured to control operation of an engine of producing energy to be charged to the battery. The hybrid electric vehicle may also include a power controller configured to cut off power supply to a component unnecessary for maintaining the sleep environment of the driver.

BRIEF DESCRIPTION OF THE DRAWINGS

The above and other objects, features and advantages of the present disclosure should be more apparent from the following detailed description taken in conjunction with the accompanying drawings, in which.

DETAILED DESCRIPTION

Figure 1:
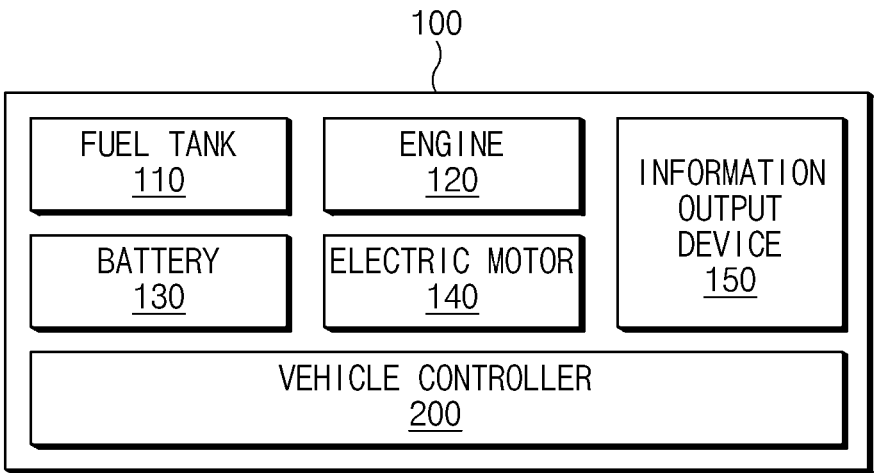
FIG. 1 is a block diagram showing an electric vehicle according to an embodiment of the present disclosure.

Hereinafter, embodiments of the present disclosure are described in detail with reference to the accompanying drawings. In the accompanying drawings, the identical or equivalent components are designated by the identical reference numeral even when they are displayed on different drawings. Further, in describing the embodiment of the present disclosure, a detailed description of the related known configuration or function is omitted when it is determined that it interferes with the understanding of the embodiment of the present disclosure.

In describing the components of the embodiments according to the present disclosure, terms such as first, second, A, B, (a), (b), and the like may be used. These terms are merely intended to distinguish the components from other components. The terms do not limit the nature, order, or sequence of the components. Unless otherwise defined, all terms including technical and scientific terms used herein have the same meaning as commonly understood by those having ordinary skill in the art to which this disclosure pertains. It should be further understood that terms, such as those defined in commonly used dictionaries, should be interpreted as having a meaning that is consistent with their meaning in the context of the relevant art and should not be interpreted in an idealized or overly formal sense unless expressly so defined herein.

When a component, device, element, or the like of the present disclosure is described as having a purpose or performing an operation, function, or the like, the component, device, or element should be considered herein as being "configured to" meet that purpose or perform that operation or function.

Hereinafter, embodiments of the present disclosure are described in detail with reference to FIGS. 1-9.

FIG. 1 is a block diagram showing an electric vehicle, according to an embodiment of the present disclosure.

An electric vehicle may be an electric vehicle that includes a battery capable of supplying electric energy to a driving motor and storing electric energy generated by regenerative braking in the driving motor. The electric vehicle may also be a hybrid electric vehicle that may include both the battery and an engine, travel by supplying the electric energy stored in the battery to an electric motor during departure and travel at a low speed, and perform hybrid travel in which the engine and the electric motor operate together in a remaining section. The hybrid electric vehicle includes a hybrid electric vehicle in a narrow sense that may inject fossil fuel only into a fuel tank and a plug-in hybrid electric vehicle that may not only inject the fossil fuel into the fuel tank, but also directly charge the electric energy into the battery. An electric vehicle 100 in FIG. 1 may correspond to a hybrid electric vehicle in a broad sense.

Referring to FIG. 1, the electric vehicle 100 may include a fuel tank 110, an engine 120, a battery 130, an electric motor 140, an information output device 150, and a vehicle controller 200.

The fuel tank 110 may be substantially the same as a tank for storing the fossil fuel in an internal combustion engine vehicle.

The engine 120 may produce electric energy using fossil fuel stored in the fuel tank 110 and supply the electric energy to the battery 130, and may directly drive the electric vehicle 100 using the fossil fuel stored in the fuel tank 110.

The battery 130 may include at least one battery module. The at least one battery module may include a plurality of battery cells. The battery 130 may store the electric energy generated using the fossil fuel by the engine 120, and may store the electric energy generated via the regenerative braking by the electric motor 140.

The electric motor 140 may drive the electric vehicle 100 using the electric energy stored in the battery 130. Because, in an embodiment, an energy efficiency of the electric motor 140 is about 50%, which is higher than an energy efficiency of the engine 120, which is about 15 to 30%, when it is inefficient to drive with the engine 120 in a travel environment of the electric vehicle 100, the electric vehicle 100 may be driven via the electric motor 140. For example, a fuel efficiency may be increased by minimizing operation of the engine 120 in a congested section or during the low-speed travel. In a travel environment that requires acceleration or high output, the engine 120 may be operated to compensate for output of the electric motor 140, so that the travel may be achieved. During braking or when traveling a downhill, the electric motor 140 may serve as a generator that converts surplus kinetic energy into the electric energy and supplies the converted electric energy to the battery 130.

The information output device 150 may include an AVN (audio, video, navigation) and/or a cluster. The information output device 150 may display travel information of the electric vehicle 100. The travel information may include, for example, one or more of information on a route guidance, data obtained by analyzing a brain wave of a driver in real time, or information on a current travel speed and a current travelable distance. In the navigation function of the information output device 150, the driver may link or register a portable terminal device to the information output device 150. When the portable terminal device is linked or registered to the information output device 150, the information output device 150 may be viewed as also including the portable terminal of the driver.

The vehicle controller 200 may control various equipment of the vehicle including the engine 120 and the battery 130. The vehicle controller 200, according to an embodiment, is described in more detail below with reference to FIG. 2 to avoid duplication of description.

Figure 2:
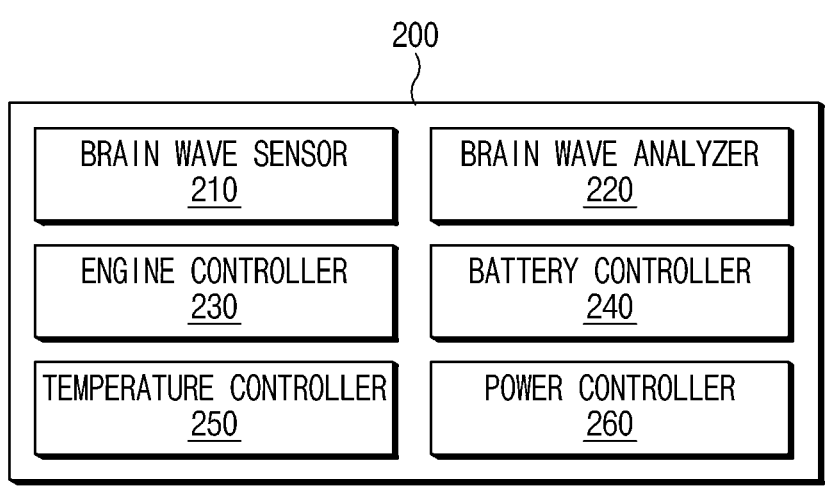
FIG. 2 is a block diagram showing a vehicle controller that may be used with the electric vehicle of FIG. 1, according to an embodiment.

FIG. 2 is a block diagram showing an example of a vehicle controller shown in FIG. 1, according to an embodiment.

Referring to FIGS. 1 and 2, a vehicle controller 200 in FIG. 2 may correspond to the vehicle controller in FIG. 1 (200 in FIG. 1). The vehicle controller 200 may include a brain wave sensor 210, a brain wave analyzer 220, an engine controller 230, a battery controller 240, a temperature controller 250, and a power controller 260.

The brain wave sensor 210 may sense a brain wave of the driver. The brain wave is biometric information measured because of constructive interference that occurs in micro-current of nerve cells when brain is activated. The brain wave shows different characteristics in an activated state of the nerve cells, so that activity of the brain may be measured using the brain wave. Because human physical activity decreases in a sleep state, the brain waves measured, respectively, in the sleep state and a non-sleep state have different characteristics. For example, although there may be differences among individuals, the brain wave generally has a frequency in a range from 8 to 12 Hz in the non-sleep state, but may have a frequency in a range from 2 to 7 Hz when entering the sleep state. As the sleep state is maintained, a slow brain wave having a frequency equal to or lower than 2 Hz may be measured. Further, as a ratio at which the slow brain wave is measured increases, a degree of sleep may deepen. Such brain wave may be sensed by attaching a number of electrode to the scalp, where the number of electrodes may be equal to or greater than one. The brain wave sensor 210 may include predetermined equipment including the electrode for sensing the brain wave of the driver.

The brain wave analyzer 220 may analyze the brain wave sensed by the brain wave sensor 210. In an embodiment, the brainwave analyzer, also known as an EEG (electroencephalogram) analyzer, is a device or software system designed to analyze and interpret the electrical activity of the brain. A method for analyzing the brain wave may include, for example, analyzing a ratio of portions of the sensed brain wave with the low frequency, and determining whether the slow brain wave (e.g., with the frequency equal to or lower than 2 Hz) having the frequency lower than that in the non-sleep state is generated and whether a ratio thereof increases. In addition, the brain wave analyzer 220 may learn a model for arbitrarily dividing sleep stages and classifying the sleep stages, and may analyze whether the driver is in the sleep state and/or is in a state requiring sleep via comparison with the brain wave sensed by the brain wave sensor 210 based on the learned model. The brain wave analyzer 220 may continuously perform the brain wave analysis, and may transmit result data obtained via the continuous brain wave analysis to the information output device 150. The result data may, for example, include data that quantifies a degree to which the driver needs to sleep, the frequency of the brain wave being measured, and whether the driver needs to sleep. The data that quantifies a degree to which the driver needs to sleep may include, for example, data on the sleep stages quantified such that a current drowsy state of the driver is identified by dividing the sleep stages into stages, e.g., 1 to 5, for a degree of drowsiness to increase from the stage 1 to the stage 5 and by classifying the non-sleep state to be a stage zero (0).

As an example of the data that quantifies the degree to which the driver needs to sleep, the stage 1 may be a stage requiring attention in which the driver intermittently yawns, the stage 2 may be a stage requiring the sleep in which the driver is intermittently drowsy, the stage 3 may be a dangerous stage in which a drowsiness frequency of the driver has increased, the stage 4 may be a stage in which the driver is in a light sleep state, and the stage 5 may be a stage in which the driver is in a deep sleep state.

The engine controller 230 may control the engine 120 to drive the electric vehicle 100. In addition, the engine controller 230 may control the engine 120 to convert the fossil fuel stored in the fuel tank 110 into the electric energy and supply the electric energy to the battery 130 using a generator connected to the engine 120 or included in the engine 120.

The battery controller 240 may control the battery 130 to store the electric energy received from the engine 120 and the electric energy generated via the regenerative braking by the electric motor 140. The battery controller 240 may identify a state of charge (SOC) of the battery and determine whether charging of the battery 130 is required. When the battery 130 needs to be charged, the battery controller 240 may calculate an amount of electric energy to be converted in the engine controller 230, and the engine controller 230 may control the engine 120 to produce the electric energy based on the calculated amount of electric energy.

The temperature controller 250 may control an air conditioning system of the electric vehicle 100. The air conditioning system may include a cooling system and a heating system. The cooling system may include a blower, an evaporator, an air conditioner compressor, and a DC voltage motor, for example. The heating system may include a heater and cooling water. The heater may be, for example, a PTC heater. In the cooling system, when air is introduced from the blower to the evaporator, a refrigerant may cool air, and an air conditioner compressor operated by the DC voltage motor may compress the refrigerant and discharge the refrigerant from the evaporator. Low-temperature air may be introduced into the electric vehicle 100 by the operation of the air conditioner compressor. The heating system may increase a temperature of the cooling water using the PTC heater, and when the warmed cooling water flows into a center of the heater, heated air may flow into the vehicle.

The power controller 260 may control power and voltage supplied to various electrical/electronic equipment that may be included in the electric vehicle 100. For example, the power controller 260 may include a low voltage DC-DC converter, and may allow the various electric/electronic equipment in the electric vehicle 100 and controllers that require power supply to be operated under low voltage conditions to prevent unnecessary power consumption. The power controller 260 may select electric/electronic equipment unnecessary when the electric vehicle 100 performs a specific operation, and may cut off power supplied to the unnecessary electric/electronic equipment.

Figure 3:
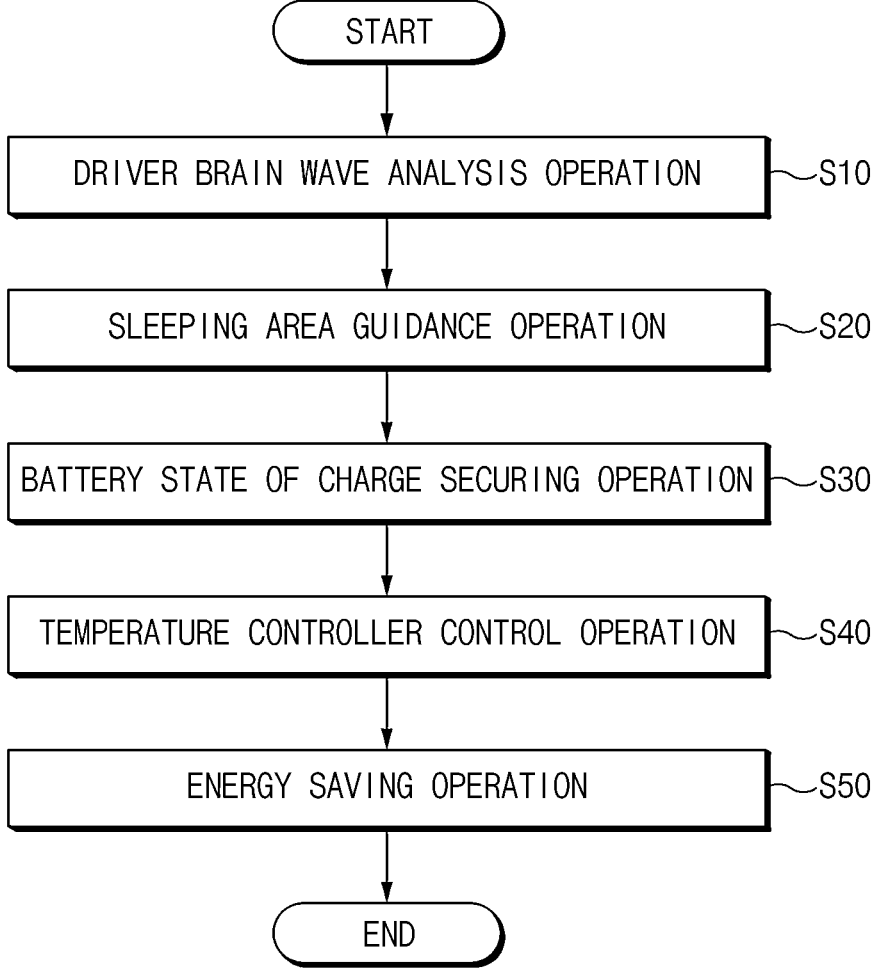
FIG. 3 is a logic diagram showing a method for controlling an electric vehicle shown in FIG. 1, according to an embodiment.

FIG. 3 is a logic diagram showing a method for controlling an electric vehicle shown in FIG. 1, according to an embodiment.

Referring to FIGS. 1-3, the method for controlling the electric vehicle 100 of the present disclosure may include a series of processes or operations. The operations may include an operation S10 of analyzing the brain wave of the driver and an operation S20 of guiding the driver to a sleeping area when it is determined that the driver needs to sleep. The operations may also include an operation S30 of securing the state of charge of the battery while moving to the sleeping area and an operation S40 of adjusting an internal temperature of the vehicle to create an optimal sleep environment (S40). The operations may further include an operation S50 of minimizing the driving of the engine 120 and maintaining the optimal sleep environment with only minimum power using the battery 130 with less noise and vibration. Details of each operation (S10-S50), according to embodiments, are described below with further reference to FIGS. 4-9 to avoid duplication of description.

Figure 4:
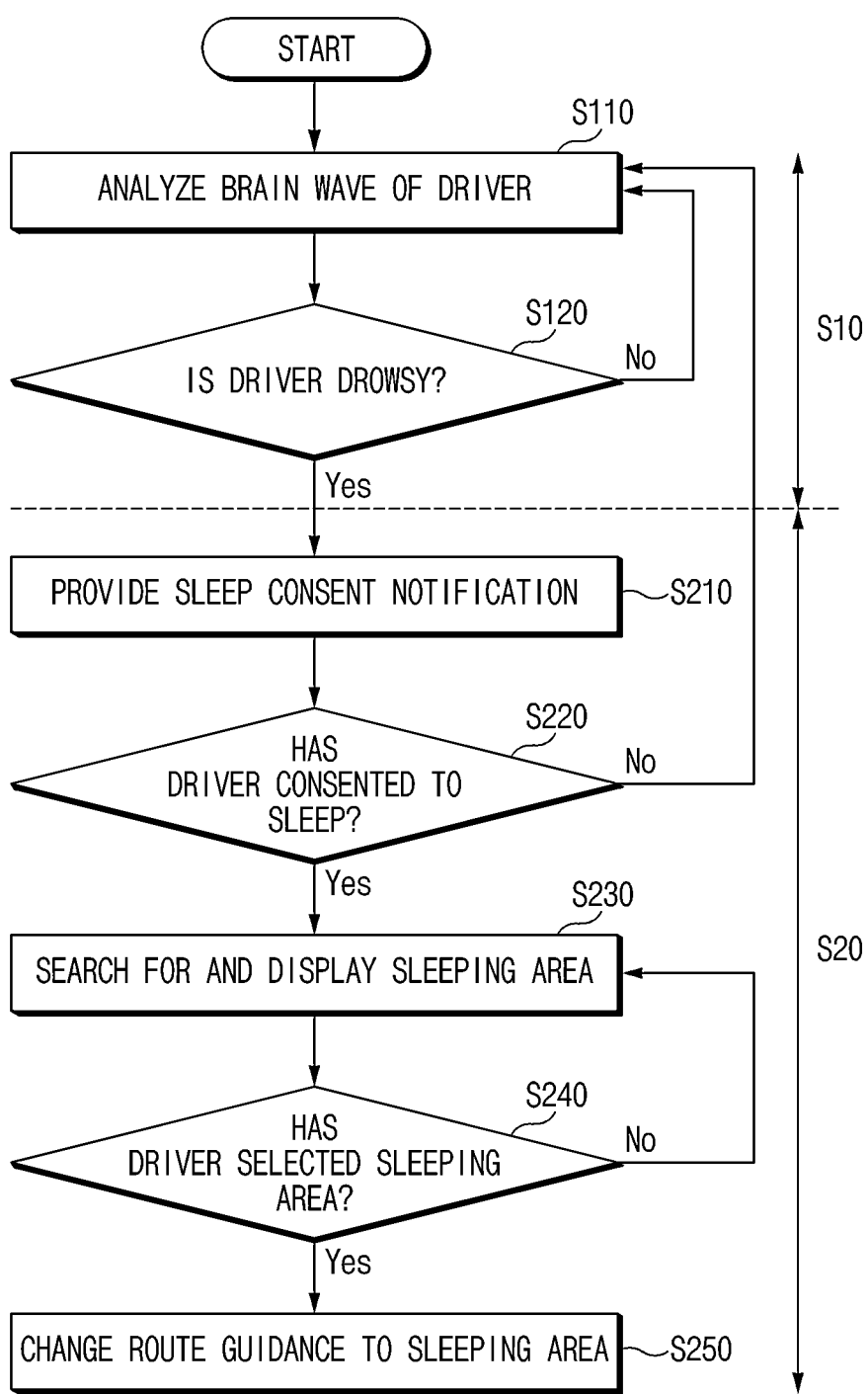
FIG. 4 is a logic diagram showing a driver brain wave analysis operation and a sleeping area guidance operation of the method of FIG. 3 in more detail, according to an embodiment.

FIG. 4 is a logic diagram showing an embodiment of a driver brain wave analysis operation and a sleeping area guidance operation shown in FIG. 3 in more detail.

Referring to FIGS. 1-4, in the driver brain wave analysis operation S10, the brain wave sensor 210 may sense the brain wave of the driver, and, in an operation S110, the brain wave analyzer 220 may analyze the sensed brain wave of the driver. In an operation S120, the brain wave analyzer 220 may analyze the brain wave of the driver to determine whether a current state of the driver is a state requiring the sleep or is the drowsy state. The state requiring the sleep may, for example, include the stage 1 requiring the attention in which the driver intermittently yawns and the stage 2 requiring the sleep in which the driver is intermittently drowsy among the stages 1 to 5 in the embodiment of the description of FIG. 2. The drowsy state may include the dangerous stage 3 in which the drowsiness frequency of the driver has increased. The stage 4 in which the driver is in the light sleep state. The stage 5 in which the driver is in the deep sleep state.

The classification may be made including the stage 2, which is the stage requiring the sleep in which the driver is intermittently drowsy. Data analyzed by the brain wave analyzer 220 may be provided to the information output device 150, and the information output device 150 may provide the analyzed data to the driver.

When it is determined as a result of identifying, by the brain wave analyzer 220, the current state of the driver that the driver is not drowsy (NO in the operation S120), the brain wave of the driver may be analyzed again in the operation S110.

In the sleeping area guidance operation S20, when it is determined as the result of identifying, by the brain wave analyzer 220, the current state of the driver that the driver is drowsy (YES in the operation S120), the information output device 150 may, in an operation S210, provide a sleep consent notification to the driver. The sleep consent notification, which may be a notification that may be provided to the driver audibly or visually, may be a notification that provides the driver with the fact that the sleep may be necessary because the driver is currently in the drowsy state. When the sleep consent notification is provided to the driver, the driver may or may not consent to enter a sleep preparation stage. A consent method may be, for example, a method in which the driver directly presses a consent button when a notification window containing the consent button is displayed on a display screen included in the information output device 150. The sleep preparation stage, which is a state that is entered under the consent of the driver, may be a stage that may include subsequent operations S230-S250.

When the driver does not consent to enter the sleep preparation stage (NO in an operation S220), the brain wave of the driver may be analyzed again in the operation S110.

When the driver consents to enter the sleep preparation stage (YES in the operation S220), the information output device 150 may, in an operation S230, search for a sleeping area and provide the searched result to the driver. The information output device 150 may search for a sleeping area within a predetermined range based on a current location of the driver and the electric vehicle 100 with the driver on board, and provide the found result to the driver. The predetermined range may be set based on, for example, a distance away from the current location. As another example, the predetermined range may be set based on an estimated time of arrival when departing from the current location. When there is no sleeping area within the predetermined range as the result of searching for the sleeping area within the predetermined range, the information output device 150 may search again by setting the predetermined range wider. When at least one sleeping area is identified as the result of searching, by the information output device 150, within the predetermined range, the information output device 150 may provide a notification that allows the driver to select one of the at least one identified sleeping area. The notification that allows the driver to select may include an option instructing the driver to re-search the sleeping area.

In an operation S240, it may be determined whether the driver has selected the sleeping area, or has made a selection instructing the re-search, in response to the notification for selecting the sleeping area.

When the driver instructs to re-search the sleeping area (NO in the operation S240), the information output device 150 may search for the sleeping area again by setting the predetermined range wider. When the information output device 150 searches for the sleeping area, the driver may arbitrarily change search criteria setting and arbitrarily change the predetermined range to induce the information output device 150 to search.

When the driver selects one of the sleeping areas (YES in the operation S240), the information output device 150 may, in an operation S250, change the route guidance to the selected sleeping area when there is the existing route guidance, and may start the route guidance to the sleeping area when there is no existing route guidance.

Figure 5:
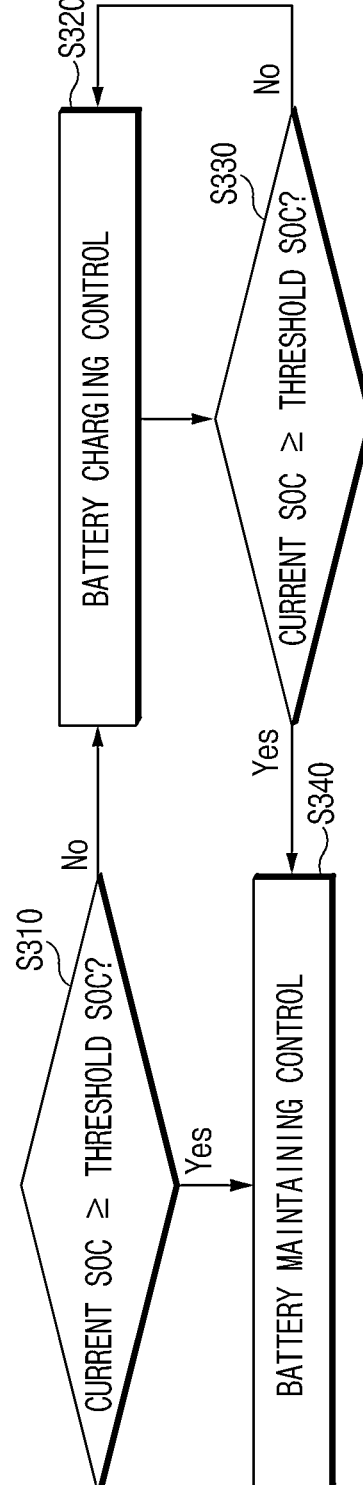
FIG. 5 is a logic diagram showing a battery state of charge securing operation of the method of FIG. 3 in more detail, according to an embodiment.

FIG. 5 is a logic diagram showing an embodiment of a battery state of charge securing operation shown in FIG. 3 in more detail.

Referring to FIGS. 1-3 and 5, in the battery state of charge securing operation S30, the battery controller 240 may, in an operation S310, determine whether the battery state of charge (hereinafter, a battery SOC) is equal to or greater than a predetermined threshold value. The state of charge (SOC) may be a numerical value expressing a current battery capacity compared to a total battery capacity in a percentage. The predetermined threshold value may be, for example, 90%.

When the battery controller 240 determines that the current battery SOC is equal to or greater than the predetermined threshold value (YES in the operation S310), the battery controller 240 may set the current battery SOC to an upper limit value of an SOC area with a good battery efficiency and perform a subsequent operation. The upper limit value of the SOC area with the good battery efficiency may mean a boundary value of a battery charge limiting SOC. When the battery SOC remains too low or too high, it may have a negative impact on a future battery life and the battery efficiency compared to a case in which the battery SOC is maintained at about 60%. A battery SOC region that may have a negative impact on the future battery life and the battery efficiency may correspond to the battery charge limiting SOC region. For example, when the life and the efficiency of the battery decrease in a case in which the battery SOC equal to or higher than 95% is maintained, the 95% may correspond to the battery charge limiting SOC. The subsequent operation may include the temperature controller control operation S40, for example.

When the battery controller 240 determines that the current battery SOC is smaller than the predetermined threshold value (NO in the operation S310), the battery controller 240 may, in an operation S320, perform control to charge the current battery S320. Details of operation S320, according to an embodiment, are described below with reference to FIG. 6 to avoid duplication of description.

After the operation S320 is performed, the battery controller 240 may, in an operation S330, determine whether the battery SOC is equal to or greater than the predetermined threshold value again.

When it is determined as a result of the re-determination by the battery controller 240 that the current battery SOC is still smaller than the predetermined threshold value (NO in the operation S330), the battery controller 240 may perform the operation S320 again.

When it is determined as the result of the re-determination by the battery controller 240 that the current battery SOC is equal to or greater than the predetermined threshold value (YES in the operation S330), the battery controller may perform operation S340.

Figure 6:
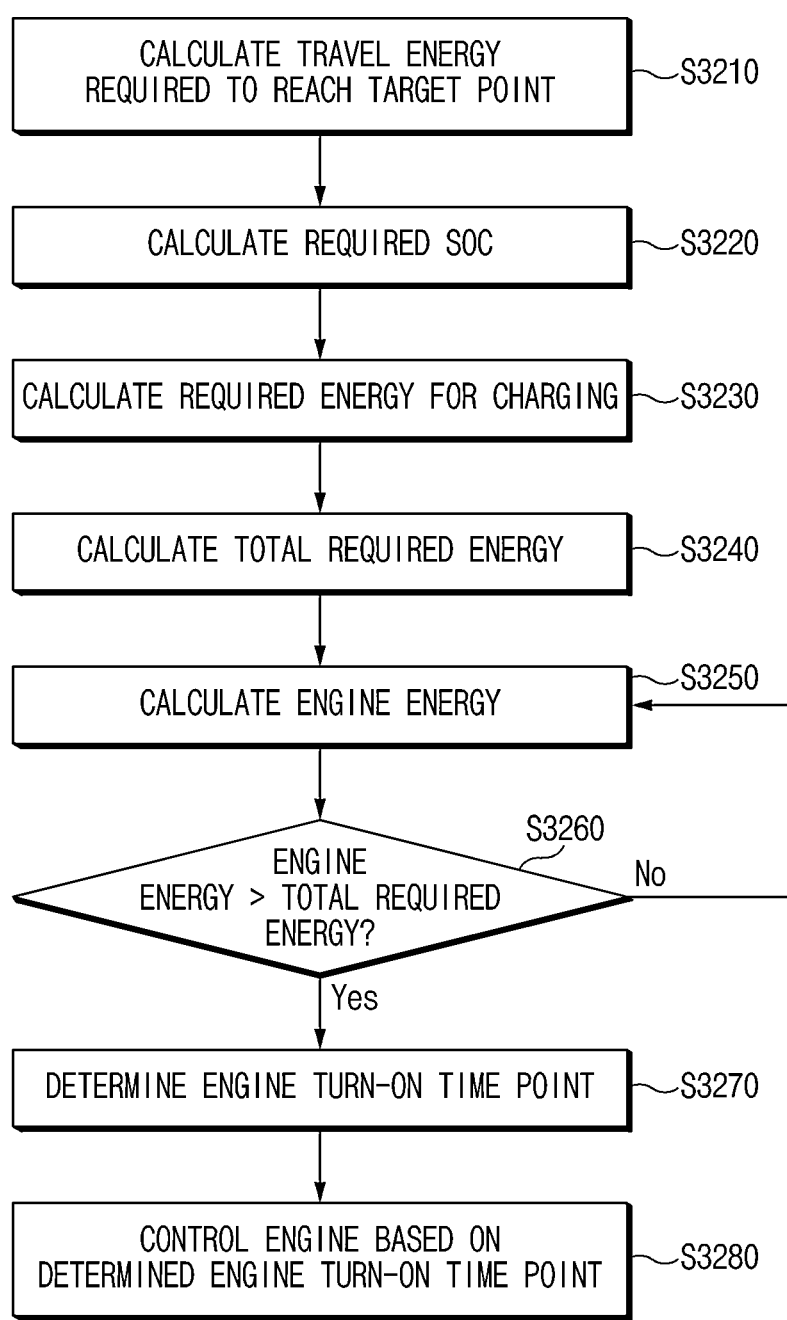
FIG. 6 is a logic diagram showing battery charging control shown in FIG. 5 in more detail, according to an embodiment.

FIG. 6 is a logic diagram showing an embodiment of battery charging control shown in FIG. 5 in more detail.

Referring to FIGS. 1-6, in the control process or operation S320 of charging the battery, the battery controller 240 may, in an operation S3210 calculate travel energy required to reach a target point. The target point may correspond to the sleeping area selected by the driver in the sleeping area guidance operation S20. The travel energy required to reach the target point may be calculated using a value representing a travel resistance of the vehicle as a time variable.

The travel resistance of the vehicle, as a generic term for forces that hinder the travel of the vehicle, may include a rolling resistance, an air resistance, a gradient resistance, and an acceleration resistance. The rolling resistance and the air resistance may correspond to resistances always considered. The gradient resistance may be additionally considered when traveling on a slope. The acceleration resistance may be considered additionally when it is not a constant-speed travel in which the acceleration of the vehicle is not 0. In consideration of each resistance element, the travel resistance of the vehicle may be obtained by calculating the respective resistance elements and summing the resistances. The travel resistance of the vehicle may be expressed in an equation for time when the travel environment and state change over time. Travel power may be calculated by multiplying the travel resistance value of the vehicle over time by the travel speed of the vehicle over time in consideration of information on a travel route to the target point (e.g., a required time, the travel speed and a speed change of the vehicle over time during the travel, a change in an inclination angle of the travel route over time, and the like). In an operation S3210, the travel energy up to the target point may be calculated according to Equation 1 by integrating the travel power with a travel time.

$$E_{drive} = \int_0^T ((R(t) \times V(t)) \times n_{TM} \times n_{mot} \times n_{bat} \times n_{DT})dt \qquad \text{Equation 1}$$

In Equation 1, $E_{drive}$ may refer to the travel energy up to the target point, $R(t)$ may refer to the travel resistance of the vehicle over time, $V(t)$ may refer to the travel speed over time, $n_{TM}$ may refer to a transmission efficiency, $n_{mot}$ may refer to efficiency of the electric motor 140, $n_{bat}$ may refer to efficiency of the battery 130, and $n_{DT}$ may refer to efficiency of a driving system. 'T', which corresponds to an upper end of an integration interval, may be an estimated time required to arrive at the target point. In addition, a $R(t) \times V(t)$ value may correspond to the travel power. The battery controller 240 may calculate the travel energy required to reach the target point based on Equation 1.

In an operation S3220, the battery controller 240 may calculate a required SOC of the battery 130. The required SOC may be calculated according to Equation 2 by subtracting the current SOC from a target SOC, where the target SOC may be, for example, a predetermined threshold value 'A'.

$$\text{required } SOC = \text{target } SOC - \text{current } SOC \qquad \text{Equation 2}$$

In an operation S3230, the battery controller 240 may calculate required energy for charging. The energy required for the charging may be calculated according to Equation 3 by multiplying the required SOC value derived in the calculation process by the battery capacity and dividing by 100.

$$\text{energy required for charging} = \qquad \text{Equation 3}$$
$$\text{required } SOC \times \text{battery capacity} \div 100$$

In an operation S3240, the battery controller 240 may calculate total required energy according to Equation 4 by adding the travel energy up to the target point and the energy required for the charging respectively derived from Equations 1 and 3.

total requried energy = travel energy up to target point + energy required for charging    Equation 4

In an operation S3250, the battery controller 240 may calculate engine energy as shown in Equation 5 below by integrating engine power over time with time:

$$E_{engine} = \int_0^T (P(t))dt \qquad \text{Equation 5}$$

In Equation 5, $E_{engine}$ may correspond to the engine energy, 'T' may correspond to the time required to reach the target point, and P(t) may correspond to the engine power.

In an operation S3260, the battery controller 240 may compare the total required energy with the engine energy respectively derived from Equations 4 and 5.

When the engine energy in S3250 is not greater than the total required energy calculated in the operation S3240 (NO in an operation S3260), the battery controller 240 may perform operation S3250 again.

When the engine energy in S3250 is greater than the total required energy in S3240 (YES in the operation S3260), at least one of the battery controller 240 or the engine controller 230 may, in an operation S3270, determine a turn-on time point of the engine 120. Hereinafter, for convenience of description, a description is made based on an embodiment in which the operation S3270 is performed by the battery controller 240.

When the turn-on time point of the engine 120 is determined in an operation S3270, the engine controller 230 may, in an operation S3280, control on/off of the engine 120 based on the determined turn-on time point of the engine 120.

A method for determining the turn-on time point of the engine 120, according to an embodiment, is described below with further reference to FIG. 7 to avoid duplication of description.

Figure 7:
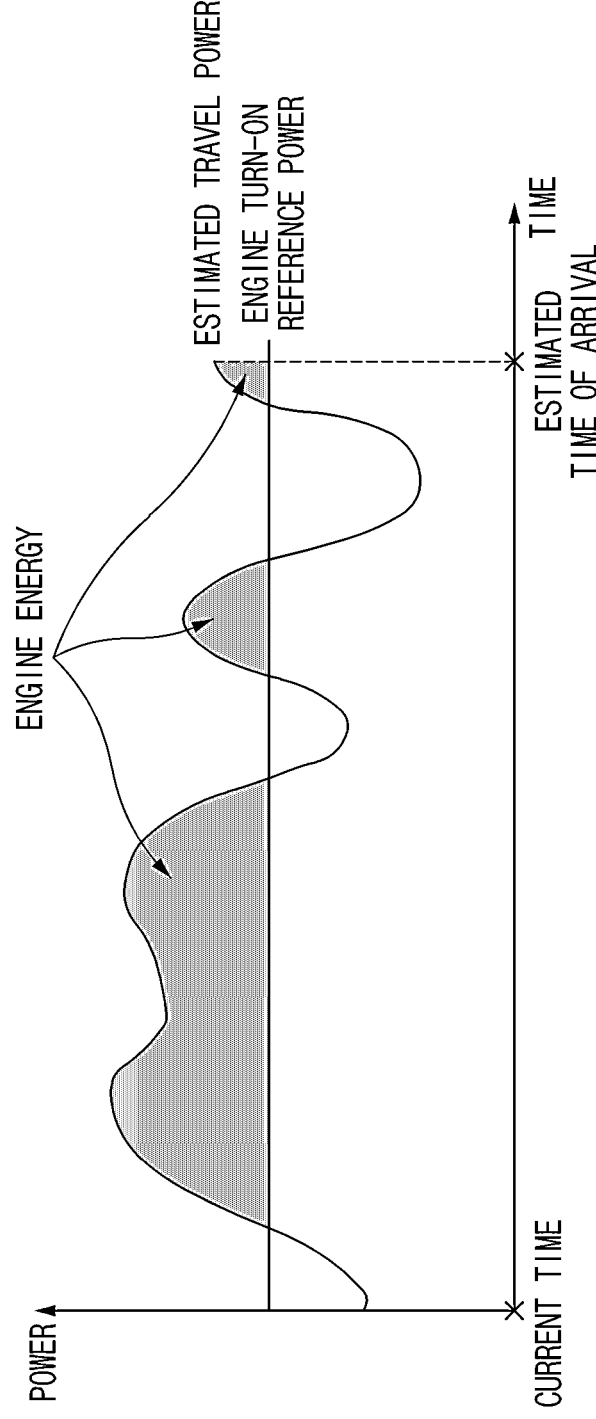
FIG. 7 is a graph showing a method for determining turn-on reference power of an engine in an embodiment of battery charging control shown in FIG. 5, according to an embodiment.

FIG. 7 is a graph showing an embodiment of a method for determining turn-on reference power of an engine in an embodiment of battery charging control shown in FIG. 5.

Referring to FIGS. 1, 6, and 7, the operations S3260 and S3270 of determining the turn-on reference power of the engine 120 may include a process of integrating, by the battery controller 240, a difference between the estimated travel power and an arbitrary power over time in a time region in which the estimated travel power of the electric vehicle 100 is greater than the arbitrary power. A result value calculated via the integration process may be the same as an area size of an area (the engine energy) shaded in FIG. 7, and the estimated travel power may be substantially equal to the R(t)×V(t) in Equation 1 described above with reference to FIG. 6. In the meaning of the shaded area (the engine energy), for example, when the arbitrary power value is 20 kW, in a time region in which the estimated travel power is equal to or greater than 20 kW, the engine 120 may be turned on to supplement the travel power by an amount required excluding 20 kW. Energy supplied from the engine 120 as the travel power is supplemented may correspond to a width of the shaded area (the engine energy). When the area size of the shaded area (the engine energy) is smaller than the total required energy calculated according to Equation 4 above, the battery controller 240 may, in an operation S3250, lower the arbitrary power value to calculate the area size of the shaded area (the engine energy) again. The battery controller 240 may determine the lowered arbitrary power value as the turn-on reference power of the engine 120 when the shaded area (the engine energy) is equal to or greater than the total required energy as a result of the recalculation. In an operation S3270, the battery controller 240 may determine a time region in which the estimated travel power is equal to or greater than the determined turn-on reference power of the engine 120 as the time point at which the engine 120 is turned on.

Figure 8:
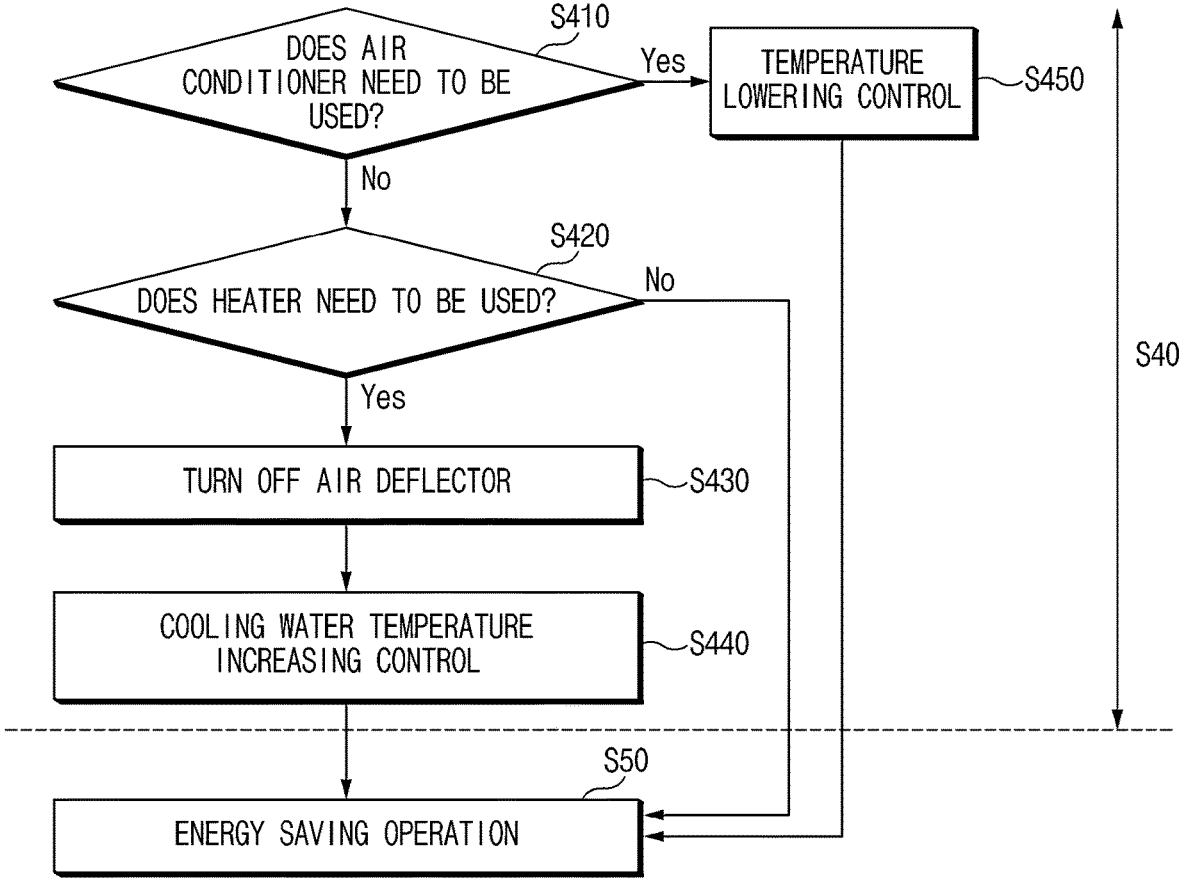
FIG. 8 is a logic diagram showing a temperature controller control operation of the method of FIG. 3 in more detail, according to an embodiment.

FIG. 8 is a logic diagram showing an embodiment of a temperature controller control operation shown in FIG. 3 in more detail.

Referring to FIGS. 1-3 and 8, after having the sufficient battery SOC via the battery state of charge securing operation S30, the temperature controller 250 may control the air conditioning system to create the optimal sleep environment for the driver. The optimal sleep environment may vary depending on the season. For example, in a case of summer when the temperature is high, about 21 to 24° C. may be the optimal sleep environment. As another example, in a case of winter when the temperature is low, about 12° C. may be the optimal sleep environment. The optimal sleep environment may differ from person to person, and the temperature controller 250 may be programmed to set an optimal temperature in consideration of a temperature of external air of the electric vehicle 100. An internal temperature of the electric vehicle 100 for the optimal sleep environment may be set by the driver in the vehicle controller 200 in advance.

In an operation S410, the temperature controller 250 may determine whether an air conditioner needs to be used.

When the temperature controller 250 determines that the air conditioner needs to be used because the internal temperature of the electric vehicle 100 is higher than an optimal sleep temperature (YES in the operation S410), the temperature controller 250 may, in an operation S450, perform temperature lowering control of lowering the internal temperature of the electric vehicle 100 via the air conditioner.

When the temperature controller 250 determines that the air conditioner does not need to be used because the internal temperature of the electric vehicle 100 is equal to or lower than the optimal sleep temperature (NO in the operation S410), the temperature controller 250 may, in an operation S420, determine whether the heater needs to be used.

When the temperature controller 250 determines that the heater does not need to be used (NO in the operation S420), the temperature controller control operation S40 may be ended and the energy saving operation S50 may be activated.

When the temperature controller 250 determines that the heater needs to be used because the internal temperature of the electric vehicle 100 is lower than the optimal sleep temperature (YES in the operation S410), the temperature controller 250 may, in an operation S430, turn off an air deflector. The air deflector may be, for example, an active air flap. The air deflector may be opened and closed electronically and may have a form of a flap. The air deflector may be located on a front surface of the vehicle and opened (turned on) or closed (turned off) depending on travel conditions. As an example of opening the air deflector, when the engine 120 operates, heat is generated. Because of the heat, the temperature of the cooling water for cooling the engine 120 may rise, and the cooling water, the temperature of which has risen, may be cooled via a radiator. When the air deflector is opened to lower the temperature of the cooling water in the radiator, the temperature of the cooling water may be controlled to be lowered by inflow of external air. An example of closing the air deflector may include increasing the temperature of the cooling water. When the air deflector is closed to block the inflow of external air, the temperature of the cooling water may be maintained high.

An embodiment of the present disclosure provides a method for controlling the electric vehicle 100 that minimizes the operation of the engine 120 to increase the energy efficiency and minimizes the noise and the vibration when creating the optimal sleep environment for inducing the sleep. The temperature controller 250 may maintain the temperature of the cooling water, the temperature of which has risen, by the heat generated in the engine 120 at the turn-on time point of the engine 120 in FIG. 6. The temperature controller 250 may maintain the temperature of the cooling water to prepare for the temperature of the cooling water being gradually lowered after the engine 120 is turned off in the future. In addition, the function of turning on the engine 120 to control the temperature of the cooling water when the temperature of the cooling water drops to a temperature equal to or lower than a predetermined temperature for the temperature control of the cooling water at a conventional technical level in the field is a function inherent in a conventional vehicle. The temperature controller 250 may prevent the engine 120 from being turned on, which would interfere with the sleep, by maintaining the temperature of the cooling water high when the heater needs to be used to increase the internal temperature of the electric vehicle 100.

In an operation S440, the temperature controller 250 may perform cooling water increasing control of maintaining the temperature of the cooling water high via the turning off of the air deflector in the operation S430. When the series of temperature control processes (operations S410-S450) of the temperature controller 250 are completed, the energy saving operation S50 may be performed. Details of the energy saving operation S50, according to an embodiment, are described below with reference to FIG. 9.

Figure 9:
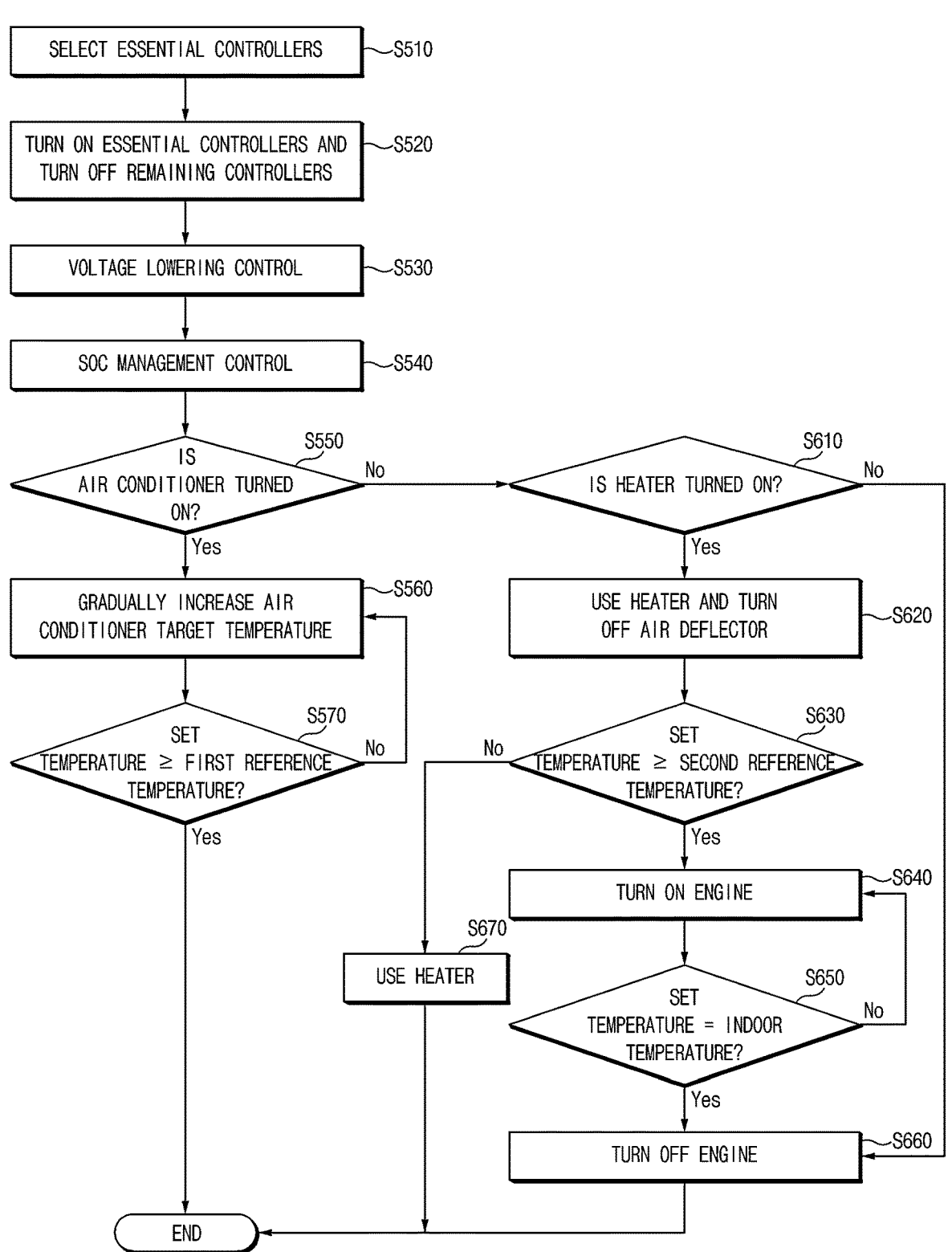
FIG. 9 is a logic diagram illustrating an energy saving operation of the method of FIG. 3 in more detail, according to an embodiment.

FIG. 9 is a logic diagram illustrating an embodiment of an energy saving operation shown in FIG. 3 in more detail.

Referring to FIGS. 1-3 and 9, the energy saving operation S50 may be performed after the electric vehicle 100 moves to the sleeping area and stops. The energy saving operation S50 may be an operation capable of minimizing energy consumed in creating and maintaining the optimal sleep environment for the driver after the electric vehicle 100 stops. to the energy saving operation S50 may include controlling the power supplied to each component of the electric vehicle 100 from the power controller 260 and creating and maintaining the optimal sleep environment while minimizing battery consumption via cooperative control of the engine controller 230, the battery controller 240, and the like centering on the temperature controller 250.

In the energy saving operation S50, the power controller 260 may, in an operation S510, select essential controllers required to create and maintain the optimal sleep environment. The essential controllers may include, for example, the engine controller 230, the battery controller 240, and the power controller 260. The power controller 260 may maintain a turn-on state by maintaining a power supply to the selected essential controllers, and may maintain a turn-off state by cutting off a power supply to the remaining controllers except for the selected essential controllers. For example, the cluster (an instrument panel) of the information output device 150 or controllers such as the brain wave sensor 210, the brain wave analyzer 220, and the like that become unnecessary based on the fact that the brain wave analysis of the driver who will sleep after stopping the vehicle may not be selected as the essential controllers and thus, may be turned off. A list of the essential controllers may be set in advance via programming.

After turning off the unnecessary controllers, the power controller 260 may, in an operation S530, perform voltage lowering control of providing low power at a level capable of maintaining a current battery state to the selected essential controllers via the low voltage DC-DC converter. When the essential controllers are turned on by supplying high voltage, the battery SOC consumption is fast, so that the voltage lowering control operation S530 may be performed to reduce the battery consumption.

When the battery SOC becomes lower than a predetermined minimum reference value, the engine 120 may be turned on because of IDLE to increase the battery SOC. The IDLE may mean that the engine 120 is in an idle state. To prevent the engine 120 from being turned on to charge the battery 130 with the idle of the engine 120, the battery controller 240 may, in an operation S540, perform SOC management control of setting the predetermined minimum reference value to the lowest SOC limit value. The lowest SOC limit value may be, for example, a value included in a range from 0 to 25%.

Under the low voltage control of the power controller 260, the temperature controller 250 may create and maintain the optimal sleep environment for the driver using less power. In an operation S550, the temperature controller 250 may determine whether the air conditioner is turned on in the temperature controller control operation S40.

When the turn-on state of the air conditioner is maintained (YES in the operation S550), because operation of the air conditioner may be a factor that increases a decreasing speed of the battery SOC, the temperature controller 250 may, in an operation S560, reduce the decreasing speed of the battery SOC by adjusting an indoor target temperature of the air conditioner to a temperature higher than that in the temperature controller control operation S40 considering that a body temperature may drop while the driver sleeps. For example, the temperature controller 250 may, in the operation S560, gradually increase the preset target temperature of the air conditioner at a constant speed for each hour (e.g., a ° C./minute). As an example, when the preset target temperature of the air conditioner is 22° C. and the current indoor temperature is 24° C., the temperature controller 250 may increase the target temperature of the air conditioner at a rate of 0.02° C. for each minute.

The temperature controller 250 may determine the target temperature (hereinafter, a first reference temperature) higher by the certain ratio (e.g., b %) than the preset target temperature. The first reference temperature, which is the temperature increased by the constant ratio relative to the temperature, may be set as a final target temperature. In an operation S570, the temperature controller 250 may determine whether a set temperature, which may be rising at a constant speed for each hour relative to the preset target temperature of the air conditioner, has reached the final target temperature. For example, when the certain ratio is 5%, because the preset target temperature of the air conditioner is 22° C., the temperature increased by 5% becomes 23.1° C. (an example of the first reference temperature). Therefore, in the above example, when the target temperature of the air conditioner is increased at the rate of 0.02° C. for each minute, the temperature of 23.1° C. is reached after 55 minutes, and the target temperature of the air conditioner may be maintained at 23.1° C. after 55 minutes have elapsed.

When the rising target temperature becomes equal to or higher than the final target temperature (YES in the operation S570), the temperature controller 250 may maintain the current temperature target, and the power controller 260 may supply minimum power such that the current control state may be maintained.

When the air conditioner is turned off or when the target temperature is quickly reached, causing the air conditioner to turn off in the temperature controller control operation S40 (NO in the operation S550, the temperature controller 250 may perform an operation S610 to determine whether the heater is turned on.

When the turn-off state of the heater is maintained (NO in the operation S610), the engine controller 230 may, in an operation S660, turn off the engine 120 or maintain the turn-off state.

When the turn-on state of the heater is maintained (YES in the operation S610), the temperature controller 250 may, in an operation S620, use the heater to increase the internal temperature of the electric vehicle 100 without turning on the engine 120 and may turn off the air deflector. The heater may be, for example, the PTC heater. When the heater is operated to supply warm air into the electric vehicle 100, the temperature controller 250 may turn off the air deflector to block the inflow of external air to prevent external air that may cool the warm air from flowing into the electric vehicle 100.

In an operation S630, the temperature controller 250 may determine whether a target temperature set in the heating system including the heater is greater than a value (C) (hereinafter, a second reference temperature) obtained by adding a predetermined temperature 'c' to the current temperature. It may be understood that the predetermined temperature 'c' is a temperature increase with which it may be expected that the current temperature reaches the target temperature set in the heating system only by the operation of the heater without increasing the temperature of air inside the electric vehicle 100 because of the heat that may be generated as the engine 120 is turned on. Even when the current temperature has not yet reached the target temperature preset in the heater, the temperature controller 250 may, in the operation S630, determine whether the second reference temperature is greater than the target temperature (C) preset in the heater in order to determine whether to turn on the engine 120 in a subsequent process. The 'c' may usually be set to around 3 (C). For example, the 'c' may be a value equal to or greater than 2.5 and equal to or smaller than 3.5.

When the second reference temperature is greater than or equal to the preset target temperature (NO in the operation S630), the temperature controller 250 may, in an operation S670, continuously increase the current temperature only with the heater without turning on the engine 120 by the cooperative control of the engine controller 230, and the series of processes for creating the optimal sleep environment may be ended.

When the second reference temperature is still lower than the preset target temperature (YES in the operation S630), because this corresponds to a state in which the current temperature is still much lower than the preset target temperature, the temperature controller 250 may, in an operation S640, increase the current temperature more quickly by generating the heat via the turn-on of the engine 120. After turning on the engine 120 in the operation S640, the temperature controller 250 may, in an operation S650, determine whether the current temperature is equal to the preset target temperature. In an operation S660, when the current temperature reaches the preset target temperature, the temperature controller 250 may turn off the engine 120.

In an embodiment of the present disclosure, to prevent the sleep environment of the driver from deteriorating as the engine 120 is turned on, hybrid control of the heater during the operation of the air conditioner requiring the operation of the engine 120, and the turn-on of the engine 120 for learning during the stop may be limited.

The description above is merely illustrative of the technical idea of the present disclosure, and various modifications and changes may be made by those having ordinary skill in the art without departing from the essential characteristics of the present disclosure.

The embodiments disclosed in the present disclosure are not intended to limit the technical idea of the present disclosure. Rather, the embodiments disclosed in the present disclosure are described to illustrate the present disclosure. The scope of the technical idea of the present disclosure is not limited by the embodiments. The scope of the present disclosure should be construed as being covered by the scope of the appended claims, and all technical ideas falling within the scope of the claims should be construed as being included in the scope of the present disclosure.

According to embodiment of the present disclosure, provided are an electric vehicle and a method for controlling the same that prevent the accidents in advance by identifying whether the driver is actually drowsy using the brain wave analysis function and guiding the driver to the sleeping area, and maintain the optimal sleep environment and prevent the unnecessary battery consumption during the sleep after stopping in the sleeping area.

Hereinabove, although the present disclosure has been described with reference to embodiments and the accompanying drawings, the present disclosure is not limited thereto, but may be variously modified and altered by those having ordinary skill in the art to which the present disclosure pertains without departing from the spirit and scope of the present disclosure claimed in the following claims.

What is claimed is:

1. A method for controlling an electric vehicle, the method comprising:

determining whether a driver needs to sleep based on a result of analyzing a brain wave of the driver;

changing a destination to a sleeping area based on selection of the driver when it is determined that the driver needs to sleep; securing a state of charge of a battery necessary for movement to the sleeping area and the sleep of the driver; and minimizing power consumption of a selected controller when controlling a sleep temperature of the driver, wherein minimizing the power consumption includes:

selecting essential controller required to create and maintain optimal sleep environment after the electric vehicle moves to the sleeping area and stops, turning off remaining controllers except for the selected controller, performing voltage lowering control of supplying power at a level capable of maintaining a battery state to the selected controller, and supplying minimum power to the selected controller after a target sleep temperature is reached.

2. The method of claim 1, wherein determining whether the driver needs to sleep includes providing a sleep consent notification.

3. The method of claim 1, wherein the sleeping area is a sleeping area within a predetermined range based on a current location.

4. The method of claim 1, wherein securing the state of charge of the battery includes determining whether to charge the battery based on a predetermined threshold value.

5. The method of claim 1, wherein securing the state of charge of the battery includes calculating an amount of energy required for charging when the battery needs to be charged.

6. The method of claim 5, wherein securing the state of charge of the battery includes determining a time point for turning on an engine to charge the battery.

7. The method of claim 1, further comprising controlling an indoor temperature of the electric vehicle and a temperature of cooling water.

8. The method of claim 7, wherein controlling the indoor temperature of the electric vehicle and the temperature of the cooling water includes controlling the indoor temperature to a temperature lower than a target indoor temperature when the indoor temperature needs to be lowered.

9. The method of claim 7, wherein controlling the indoor temperature of the electric vehicle and the temperature of the cooling water includes controlling the temperature of the cooling water to a temperature higher than a target cooling water temperature when to be increased.

10. The method of claim 1, wherein minimizing the power consumption is performed after travel of the electric vehicle is ended.

11. A hybrid electric vehicle, comprising:
a brain wave sensor configured to sense a brain wave of a driver;
a brain wave analysis device configured to determine whether the driver needs to sleep by analyzing the brain wave sensed by the brain wave sensor;
an information output device configured to change a destination to a sleeping area and guide the sleeping area when the driver needs to sleep;
a battery controller configured to control a state of charge of a battery necessary for movement to the sleeping area and maintaining a sleep environment of the driver; and
a power controller configured to cut off power supply to a component unnecessary for maintaining the sleep environment of the driver, wherein the power controller is configured to:
  select essential controller required to create and maintain optimal sleep environment after the hybrid electric vehicle moves to the sleeping area and stops, turn off remaining controllers except for the selected controller,
  perform voltage lowering control of supplying power at a level capable of maintaining a battery state to the selected controller, and
  supply minimum power to the selected controller after a target sleep temperature is reached.

12. The hybrid electric vehicle of claim 11, wherein the information output device is configured to provide a sleep necessity notification when the driver needs to sleep.

13. The hybrid electric vehicle of claim 11, wherein the information output device is configured to:
  search to identify a sleeping area within a predetermined range based on a current location, and
  provide the identified sleeping area to the driver when the driver needs to sleep.

14. The hybrid electric vehicle of claim 11, wherein the battery controller is configured to calculate an amount of energy required for charging of the battery when a current state of charge of the battery is smaller than a predetermined threshold value.

15. The hybrid electric vehicle of claim 14, further comprising:
  an engine controller configured to control an operation of an engine for supplying the energy to be charged to the battery,
  wherein the battery controller is configured to determine a time point for turning on the engine based on the calculated amount of energy for the charging.

16. The hybrid electric vehicle of claim 11, further comprising:
  a temperature controller configured to control an indoor temperature of a room where the driver is located and a temperature of cooling water of the hybrid electric vehicle.

17. The hybrid electric vehicle of claim 16, wherein the temperature controller is configured to set a target indoor temperature based on the indoor temperature of the room where the driver is located and an external temperature of the hybrid electric vehicle.

18. The hybrid electric vehicle of claim 17, wherein the temperature controller is configured to perform control to increase the temperature of the cooling water when the indoor temperature needs to be increased.

19. The hybrid electric vehicle of claim 16, further comprising:
  an engine controller configured to control operation of an engine of producing energy to be charged to the battery.

\* \* \* \* \*